US006537930B1

(12) United States Patent
Middlesworth et al.

(10) Patent No.: US 6,537,930 B1
(45) Date of Patent: Mar. 25, 2003

(54) THREE-DIMENSIONAL HIGHLY ELASTIC FILM/NON-WOVEN COMPOSITE

(75) Inventors: Jeff A. Middlesworth, Wauconda, IL (US); James W. Cree, Chesterfield, VA (US); Steve D. Bruce, Crystal Lake, IL (US)

(73) Assignee: Tredegar Film Products Corporation, Richmond, VA (US)

( * ) Notice: Subject to any disclaimer, the term of this patent is extended or adjusted under 35 U.S.C. 154(b) by 0 days.

(21) Appl. No.: 09/574,657

(22) Filed: May 18, 2000

(51) Int. Cl.$^7$ ............................................. B32B 27/12
(52) U.S. Cl. .................. 442/39; 442/328; 442/329; 442/366; 442/376; 442/382; 442/401; 428/137; 428/196; 428/198
(58) Field of Search ................. 442/328, 329, 442/366, 370, 382, 394, 401; 428/196, 198, 137

(56) References Cited

U.S. PATENT DOCUMENTS

| | | | | |
|---|---|---|---|---|
| 4,781,962 A | * | 11/1988 | Zamarripa et al. ........... | 428/137 |
| 4,938,753 A | | 7/1990 | Van Gompel et al. ... | 604/385.2 |
| 4,965,122 A | | 10/1990 | Morman ..................... | 428/225 |
| 4,981,747 A | | 1/1991 | Morman ..................... | 428/198 |
| 5,114,781 A | | 5/1992 | Morman ..................... | 428/198 |
| 5,116,662 A | | 5/1992 | Morman ..................... | 428/198 |
| 5,226,992 A | | 7/1993 | Morman ..................... | 156/62.4 |
| 5,336,545 A | | 8/1994 | Morman ..................... | 428/152 |
| 5,385,775 A | | 1/1995 | Wright ........................ | 428/284 |
| 5,399,366 A | | 3/1995 | Geddes et al. ................ | 426/87 |
| 5,441,550 A | | 8/1995 | Hassenboehler, Jr. et al. ........................ | 55/486 |
| 5,443,606 A | | 8/1995 | Hassenboehler, Jr. et al. ........................ | 55/486 |
| 5,486,411 A | | 1/1996 | Hassenboehler, Jr. et al. ........................ | 428/286 |
| RE35,206 E | | 4/1996 | Hassenboehler, Jr. et al. ........................ | 55/528 |

(List continued on next page.)

FOREIGN PATENT DOCUMENTS

| | | |
|---|---|---|
| EP | 0415758 | 3/1991 |
| EP | 0560630 | 9/1993 |
| JP | 8182704 A2 | 7/1996 |

OTHER PUBLICATIONS

Wadsworth, Ph.D, Larry C. and Charles B. Hassenboehler, Jr., Ph.D., TANDEC, The University of Tennessee. "Stretchable Fabric Technology Options.", *Nonwovens World* Spring 1994: 49, 50, 53–56.

Hassenboehler, Charles B. and Larry C. Wadsworth, TANDEC. "Expanding Roll Goods Value by Easy Stretch Processing." *Nonwovens World: IDEA 98 Show Issue* Apr. 1998: 83–88.

Copy of Form EPA/EPO/OEB Form P0152 05/91 EP Standard Search RS105624 US.

*Primary Examiner*—Elizabeth M. Cole
*Assistant Examiner*—Norca L. Torres
(74) *Attorney, Agent, or Firm*—Jenkens & Gilchrist, P.C.

(57) ABSTRACT

A three-dimensional highly elastic film/non-woven composite having a fluid and air impervious core layer and a first and second consolidated layer. The consolidated layers have unidirectional and non-unidirectional fibers. The composite is formed by laminating the air and fluid impermeable elastic core layer between the two layers of consolidated nonwovens. The resulting composite stretches only in the cross-machine direction due to the unidirectional properties of the consolidated non-woven material. The layers are then point bonded or welded together. Preferably the layers are welded by passing the composite between an ultrasonic horn and an ultrasonic bond roll having raised areas for effecting the weld points. A thin inelastic membrane is formed at each of the weld points. The welded composite may then be pre-stretched to rupture the membranes, thereby creating apertures, which makes the composite permeable.

21 Claims, 4 Drawing Sheets

U.S. PATENT DOCUMENTS

| | | |
|---|---|---|
| 5,514,470 A | 5/1996 | Haffner et al. ............... 428/343 |
| 5,529,830 A | 6/1996 | Dutta et al. ................. 428/176 |
| 5,599,366 A | 2/1997 | Hassenboehler, Jr. et al. ........................... 55/486 |
| 5,628,856 A | 5/1997 | Dobrin et al. ......... 156/244.18 |
| 5,700,255 A | 12/1997 | Curro et al. ............. 604/385.2 |
| 5,709,921 A | 1/1998 | Shawver ..................... 428/152 |
| 5,836,932 A | 11/1998 | Buell et al. ................. 604/396 |
| 5,851,935 A | * 12/1998 | Srinivasan et al. ......... 442/328 |
| 5,853,881 A | 12/1998 | Estey et al. ................. 428/373 |
| 5,938,651 A | 8/1999 | Widlund et al. ............ 604/373 |

* cited by examiner

THREE-DIMENSIONAL HIGHLY ELASTIC FILM/NON-WOVEN COMPOSITE

BACKGROUND OF THE INVENTION

1. Field of the Invention

The invention relates generally to film/non-woven composites and specifically, to a point bonded highly elastic film/non-woven composite that is made breathable after manufacture by stretching the composite to rupture inelastic membranes formed on the composite by weld points used to point bond the composite.

2. Related Art

There is a need to improve the fit and comfort of diaper products and the like in the consumer disposable market. Laminates that deliver high extensibility coupled with high elastic recovery, breathability, and tear resistance are being sought as the means to satisfy this need.

In the past, techniques used to achieve high stretch in non-woven laminates would often damage the non-woven fibers or bonds, thereby resulting in reduced laminate strength, especially tensile strength. In addition, the laminates produced by prior techniques often lack sufficient elastic recovery to function optimally in desired applications.

Breathability for these laminates have typically been generated by perforating the film before laminating the film to the non-woven. The lamination of the film to the non-woven are often performed by the use of adhesives. These adhesives have a tendency to block the holes or apertures in the laminates, thus potentially reducing desired breathability.

Breathability was also generated by perforating the film through other perforation processes, such as perforating the film after laminating the film to the non-woven. But these perforation processes result in various points of weakness on the overall laminate. The points of weakness often become tear initiation points.

In the prior art, often many cumbersome and expensive steps must be followed to create a laminate having the desired properties.

Therefore it is necessary to develop a laminate and a method for making the same that has high elasticity combined with high elastic recovery for use in disposable article market. In addition, it is desirable to develop a laminate and a method for making the same that eliminates the tear initiation points that formed on prior art laminates. There is a further need to make a laminate having a relatively high tear resistance at a predetermined stretch elongation of the laminate. Finally, there is a need to reduce the number of steps needed to create the laminate while maintaining the above-stated properties.

SUMMARY OF THE INVENTION

The present invention provides an improved film/non-woven composite that only stretches in the cross-machine direction and exhibits fluid and air permeable properties. The film/non-woven composite in one embodiment of the present invention comprises two consolidated layers laminated onto a core layer. The consolidated layers are composed of unidirectional and non-unidirectional fibers. The unidirectional and non-unidirectional fibers provide for stretchable and non-stretchable regions on the composite.

The layers of the composite are welded together at discrete points. In one embodiment, an ultrasonic horn is used to weld the composite. After welding, the following distinct regions are formed on the composite: non-welded regions, bond regions, and membrane regions. The non-welded regions are the areas of the composite surrounding the weld points. The weld points, where an actual bond forms, are amalgamated masses of polymer that are dislodged by force and thermal/fusion energy during the welding step. The membrane regions are very thin impervious membranes of polymer material that remain after the thermal/fusion energy application.

After the composite has been formed, some areas of the composite exhibit high elasticity. The composite may be stretched by an end use to tear the membranes in the membrane region and impart breathability to the film. The ratio of tensile to break in the machine direction versus the tensile to break in the cross direction of the fibers in the consolidated layers is in the range of about 3:1 to about 1.8:1.

DETAILED DESCRIPTION OF THE DRAWINGS

Figure 1:
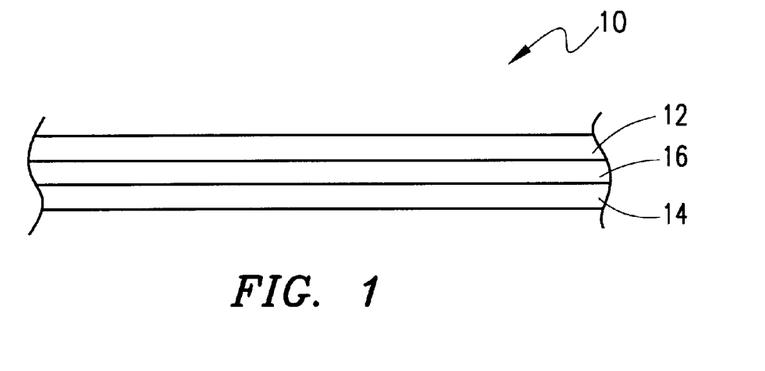
FIG. 1 is a cross-section of the film/non-woven composite of the present invention before the welding step.
Figure 2:
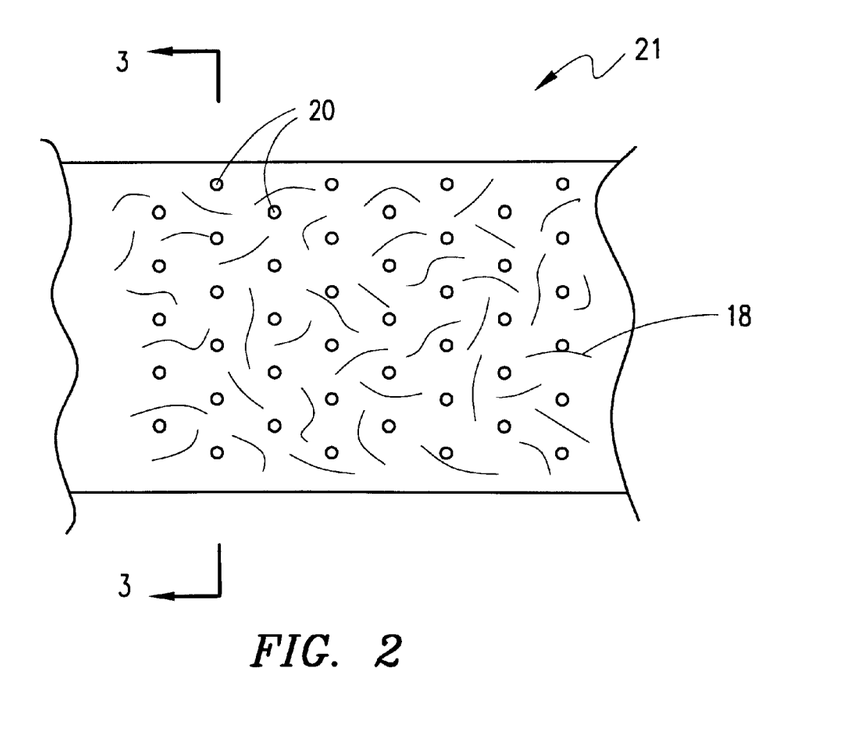
FIG. 2 is a top view of the film/non-woven composite of the composite of FIG. 1 after the welding step.

Referring to FIG. 1 there is shown a three-dimensional, highly elastic film/non-woven composite 10 that has high extensibility and a low modulus of elasticity. The composite 10 includes a first consolidated sheet 12, a second consolidated sheet 14, and an impervious film core layer 16. The consolidated sheets are composed of a spunbond fibers 18 (FIG. 2). Spunbond fibers 18 may be non-woven bicomponent or blended fibers. If the spunbond fibers 18 are bicomponent fibers, the components of the fibers 18 preferably have two distinct meltpoints. Similarly, if the sheets 12 and 14 are comprised of blended fibers, it is preferred that the blended fibers have two distinct melt points. Preferably, spunbond fibers 18 have a weight of around 15–30 gsm. The film core layer 16 may be of various materials, but the materials must be impervious to fluid and air. In one embodiment, the core layer 16 may be comprised of a multi-layer film. Alternate elastomeric films may also be used as the core layer 16, such as a single layer elastomer, or a foam layer, but such films must be comprised of fluid and/or air impervious materials.

In another embodiment, the core layer 16 is a highly-elastic compound, such as a compound involving at least one or more block co-polymers with a hydrogenated diene from the type A-B-A or A-B-A'. Usually such a compound exhibits relatively good elastic recovery or low set from stretching over 100 percent when extruded alone as a single layer. Styrene/isoprene, butadiene or ethylene-butylene/styrene (SIS, SBS, or SEBS) block copolymers are particularly useful. Other useful elastomeric compositions for use as an core layer 16 can include elastomeric polyurethanes, ethylene copolymers, such as ethylene vinyl acetates, ethylene/propylene copolymer elastomers or ethylene/propylene/diene terpolymer elastomers. Blends of these polymers alone or with other modifying elastic or non-elastomeric materials are also contemplated being useful with the present invention. In certain preferred embodiments, the elastomeric materials can comprise high performance elastomeric material such as SEBS, SBS, SIS or Kraton™ elastomeric resins from the Shell Chemical Co., which are elastomeric block copolymers.

To form the film/non-woven composite 10, first and second sheets of spunbond fibers 18 are oriented in an oven or other heating apparatus according to the teachings described in U.S. Pat. No. Re. 35,206 to Hassenboehler, Jr., et al., which is incorporated herein by reference. The result of this process is first consolidated sheet 12 and second consolidated sheet 14. The individual fibers 18 are closely packed on the sheets 12, 14 and stretch only in the cross-machine direction (i.e., anisotropic fibers). The elastic film/non-woven composite 10 (FIG. 1) is created by encapsulating the core layer 16 between the consolidated sheets 12, 14.

Figure 3:
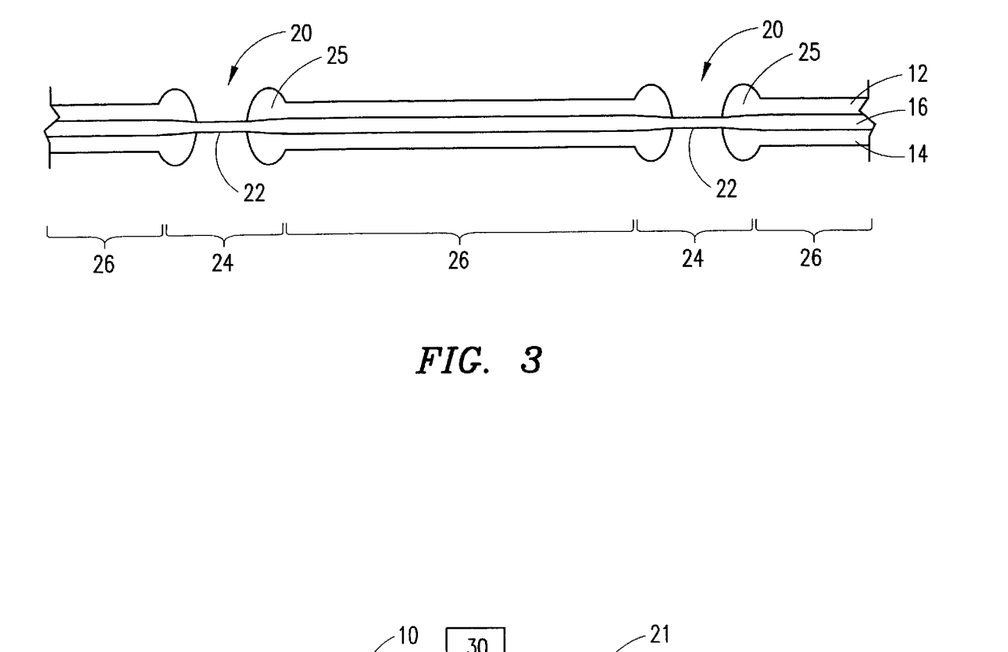
FIG. 3 is a cross-section of the composite of FIGS. 1 and 2 taken along line 3—3 of FIG. 2 after the composite has undergone the welding step.

A combination of force and thermal/fusion energy, such as ultrasonic welding or thermal contact welding, is used to combine the three layers 12, 14, 16 at discrete weld points 20 to form welded film/non-woven composite 21. (FIGS. 2 and 3). In a preferred embodiment shown in FIGS. 2 and 3, ultrasonic welding is used to form weld points 20 that join the consolidated layers 12, 14 and the impervious film core layer 16. The weld points 20 occupy between about 2% to about 10% of the total surface area of the film/non-woven composite 21. It has been found that weld points 20 having a diameter of approximately 0.75 mm and spaced in the cross-machine direction from centerline-to-centerline approximately 3.5 mm apart are desirable. Ultrasonic welding is the preferred method of forming weld points 20. Other suitable methods may be used, including thermal contact welding and point welding to create a weld points 20. A welded membrane 22 and a bond region 24 of material result from the application of weld points 20 as best seen in FIG. 3. Welded membranes 22 are very thin impervious membranes of polymer material that remain after the weld point application. The membranes 22 are essentially non-elastic. After welding, first and second consolidated sheets 12 and 14 and the impervious film core layer 16 comprise three regions. Non-welded regions 26 are the areas of the composite 21 surrounding the bond regions 24. Bond regions 24, where the actual bond forms, contain amalgamated masses 25 of polymer that are dislodged by force and thermal/fusion energy during the weld point application. The film-forming process is discussed in greater detail below.

Breathability of the welded elastic film/non-woven composite 21 results from tearing of the membranes 22. Membranes 22 are torn when composite 21 is stretched. During stretching, the membranes 22 tear because the membranes are non-elastic. Breathability is imparted to the film/non-woven composite 21 by inducing stretching in the cross-machine direction in the range of about 50% to about 200%. As an example, in the case of a 50% induction of stretching, a 1 inch sample of composite 21 becomes at least 1.5 inches long. Despite the stretching of composite 21 and the tearing of the membranes 22, the film/non-woven composite 21 provides sufficient resistance to forces, especially forces that cause elongation at the composite 21 greater than about 200%, to prevent tearing of the film/non-woven composite 21. The stretching of the film/non-woven composite 21 may occur during use, such as when an end product is stretched by the consumer or user, or prior to use at the manufacturing site, using methods known in the art. These methods include using a tentering frame, a bowed bar, or interdigitating rolls such as those described in U.S. Pat. No. 4,368,565 to Schwarz, which is incorporated herein by reference.

Figure 4:
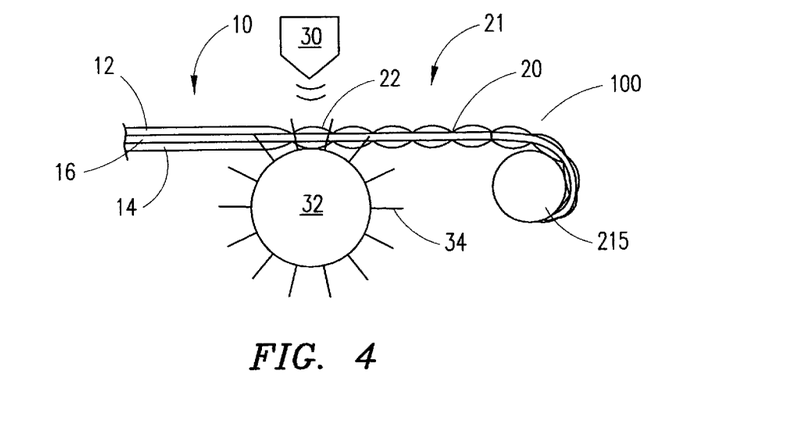
FIG. 4 is a view of the film/non-woven composite of FIGS. 1 and 3 undergoing the welding step.

Referring now to FIG. 4, the elastic film/non-woven composite 10 is shown undergoing a welding processes to form weld points 20. Weld points 20 point bond or weld the consolidated sheets 12, 14 to the impervious film core layer 16 to form welded elastic film/non-woven composite web 21. To perform ultrasonic welding, the elastic film/non-woven composite web 10 is passed between ultrasonic horn 30 and ultrasonic bond roll 32. Ultrasonic bond roll 32 has a plurality of raised areas 34. During ultrasonic welding, the mass of consolidated layers 12, 14 that are proximate to the raised area 34 of the ultrasonic bond roll 32 become molten and flow outward away from ultrasonic horn 30 to form a weld point 20. The thin layer material that remains forms membrane 22, which is surrounded by amalgamated masses 25 (FIG. 3). Membrane 22 remains impervious to fluid or air after welding. The location of membrane 22 corresponds to the individual raised areas 34 of the bond roll 32, which provide the points for the ultrasonic bonding. Raised areas 34 do not completely penetrate film/non-woven composite 10 but act as a primary channel for the energy force that is being transmitted from the ultrasonic horn 30. Without raised areas 34, the force supplied by the horn 30 across the elastic film/non-woven composite web 10 would be uniform. As a result, the raised areas 34 impart a pattern on welded film/non-woven composite 21.

The resulting welded film/non-woven composite 21 has high elasticity in the cross-machine direction, which is the direction transverse to the direction that the composite 10 and resulting welded composite 21 travel during the welding process shown in FIG. 4. Welded composite 21 resists stretching in the machine direction, which is parallel to the direction the composite 10 and resulting welded composite 21 travel during the welding process. The welded film/non-woven composite 21 has a final weight in the range of about 40–150 gsm.

After the welding process of the invention, apertures are created in the film/non-woven composite 21 by stretching composite 21 to rupture membranes 22 and the composite 21 is allowed to return to its original length.

Experimental Description

The experiment described below has been set-up to demonstrate the impact of imparting breathability on the properties of various laminates. The experiment has three steps:

1. Laminate Creation step
2. Laminate Activation steps
3. Laminate Property Quantification step.

The Laminate Creation Step involved the creation of three sample laminates, sample A, sample B, and sample C. Sample A consists of an elastic film that is ultrasonically bonded and uses Sofspan® nonwovens on both sides off the film. Sample B consists of an elastic film that is ultrasonically bonded and covered on both sides by two layers of the same Sofspan® nonwovens as sample A. In addition, each of the Sofspan® nonwoven layers was consolidated with a neck-in ratio of 2:1 before being attached to each side of the film. Sample C is the same as sample B except that each of the Sofspan® nonwoven layers was consolidated with a neck-in ratio of 3:1 before being attached to each side of the film.

In the Laminate Activation or Hole Creation Step, holes were created in samples A, B, and C by stretching the samples to various levels and allowing them to return to their original length. In this experiment, the laminates were stretched by hand. Specifically, a 1 inch mark was made on each sample and the material was stretched to a predetermined extensions. The materials were then stretched various amounts and the force required to stretch that amount was recorded.

Figure 5:
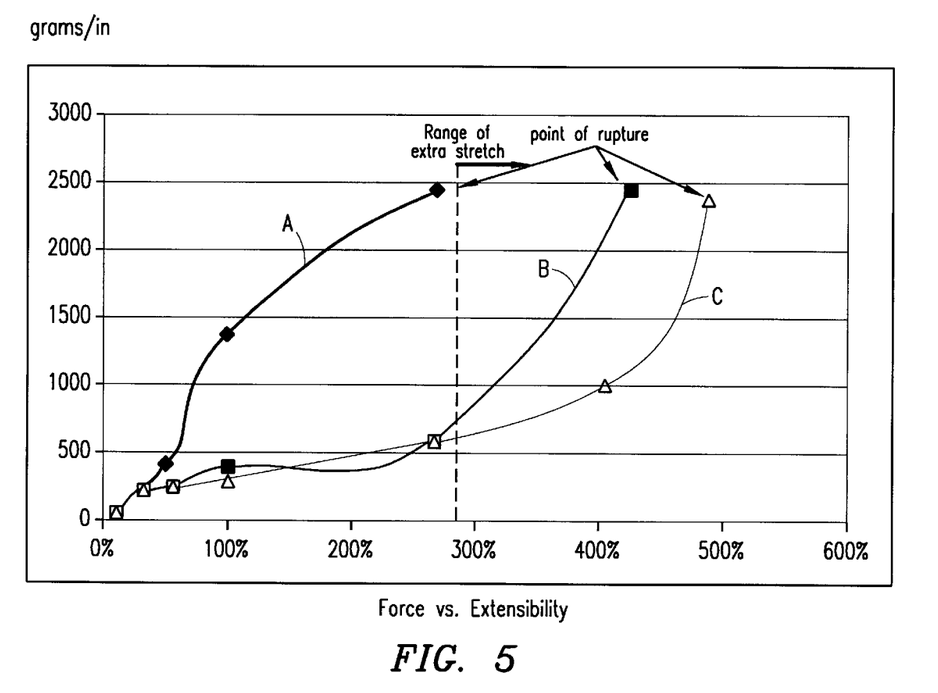
FIG. 5 is a graph showing the relationship of the force versus extensibility of consolidated and non-consolidated film/non-woven composites.

Table 1, below, and FIG. 5 show a comparison of the stretch behavior of samples A, B, and C after being pre-stretched to 100% each. The data indicates that consolidated samples B and C gained an additional 100% extensibility as compared to the non-consolidated sample A. The consolidated samples B and C required lower forces to stretch, particularly after 60% stretch. The higher force to stretch the non-consolidated samples B and C imply that the actual fibers 18 are being deformed instead of stretching. The data supports the postulate that higher deformation causes irreversible damage to the stretch matrix of the consolidated sheets. Additionally, the gain in higher extensibility by the consolidated samples B and C makes the samples easier, i.e. requires less force, to stretch the composite further as compared to the non-consolidated sample A.

before damage results to the material, e.g., sample A. Further, the consolidated film/non-woven samples B and C exhibited properties that are clearly superior to other laminates or fabrics that have been made in the past and were strained to become breathable.

As will be appreciated by those skilled in the art, the various parameters of this invention may be adjusted depending on the application, including varying the weight of the non-woven layers 12, 14, the consolidation ratio of layers 12 and 14, and the selection of the polymers for use as the impervious core film layer 16 of the elastic film/non-woven composite web.

The crux of the invention is a breathable and permeable consolidated film/non-woven composite formed by laminating an air and fluid impermeable elastic layer between two layers of consolidated non-wovens and forming an air or fluid pervious thin structure that has well-defined elasticity and selective regions of breathability without the need for using a process or apparatus to impart apertures in the film. The resulting composite allows for the formation of a high percentage of apertures from a given number of weld points by stretching the composite without damaging the structure of the composite. Additionally, the process of the invention may be practiced without using excessive thermal or fusion

TABLE 1

| Sample | Nwvn | Neck-in Ratio Initial/ Final Width | Speed Ratio Final/ Initial | Temp. Fahrenheit | Width inches | Basis WT. gsm | TD 10% grams/in | TD 25% grams/in | TD 50% grams/in | TD 100% grams/in | TD ULT force grams/in | Ult. TD Elong. % |
|---|---|---|---|---|---|---|---|---|---|---|---|---|
| A | Sofspan ® | 1:1 | 1.00 | RT | 35.125 | 118.4 | 35 | 784 | 1147 | 1412 | 2290 | 277 |
| B | Sofspan ® | 2:1 | 1.38 | 260 F. | 30.125 | 133.5 | 30 | 210 | 300 | 430 | 2306 | 441 |
| C | Sofspan ® | 3:1 | 1.75 | 260 F. | 22.125 | 142.1 | 39 | 209 | 264 | 308 | 2491 | 500 |

In the Laminate Property Quantification step, after the material was pre-stretched, the holes in each of the samples A, B, and C were counted in an a predetermined area. Next, the forces to stretch the samples in the cross machine direction and the ultimate elongation to break forces were measured.

Figure 6:
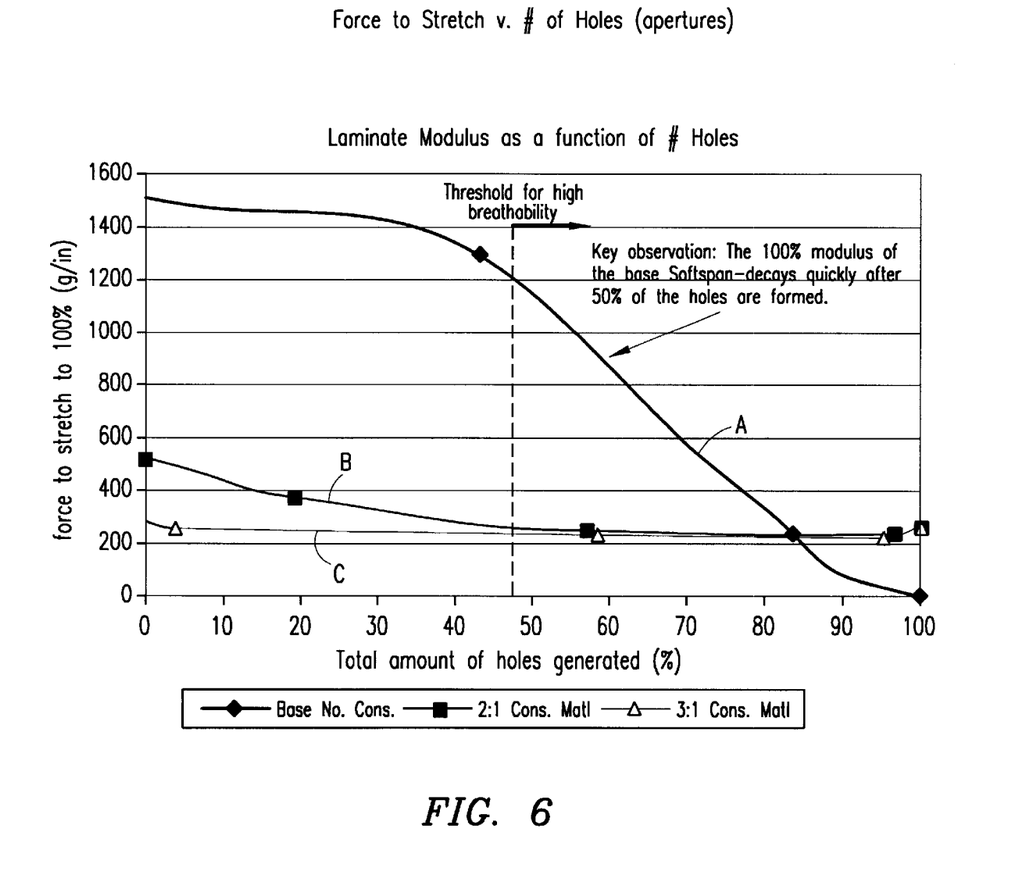
FIG. 6 is a graph showing the relationship of the force to stretch consolidated and non-consolidated composite versus the number of holes (apertures) generated.

Referring now to FIG. 6, the force to stretch versus the number of apertures generated is illustrated. In the experiment, the Samples A, B and C of the welded film/non-woven composite 21 were stretched to create apertures or pre-stretched. The apertures in each of the Samples A, B and C were then counted in a sample area to determine the percentage of membranes 22 (FIG. 3) that ruptured. Additionally, the forces to stretch the film/non-woven composite 21 to 100% elongation in the cross machine direction were measured.

By referring to FIG. 6, it can be seen that in non-consolidated film/non-woven sample A, once a 48% aperture level is reached, the overall integrity of sample A begins to decay. Additionally, both of the consolidated samples B and C experience no damage or change in their modulus properties at the 100% modulus level even though samples B and C were stretched until all of the membranes 22 had ruptured, i.e. 100% holes were created.

The data of FIG. 6 supports the conclusion that with a consolidated film/non-woven composite (samples B and C), a very high percentage of apertures may be imparted in the film/non-woven composite without damaging the network of fibers 18 or destroying the film/non-woven composite integrity. This is a great improvement over the percentage of apertures that may be formed in a non-consolidated material energy force that may damage the spikes or raised areas of the embossing roll. Further, the resulting composite stretches only in the cross-machine direction due to the unidirectional properties of the consolidated non-woven material.

While only several embodiments of the present invention have been described the present invention may also be applied to many other applications and environments. It will be obvious to those skilled in the art that various changes and modifications can be made without departing from the spirit and scope of the present invention, and it is intended to cover the claims appended hereto. All such modifications are within the scope of this invention.

What is claimed is:

1. A three dimensional highly elastic film/non-woven composite, comprising:
   a fluid and air impervious core film layer having a first side and a second side;
   a first non-woven layer point bonded by a plurality of weld points to said first side of said core layer;
   a second non-woven layer point bonded by a plurality of weld points to said second side of said core layer; and
   wherein said weld points are substantially inelastic and the weld points rupture to form apertures when the composite is stretched in a cross-machine direction to an elongation of about 200% or less.

2. The three-dimensional highly elastic film/non-woven composite of claim 1, wherein:
   said core layer comprised of a material selected of a group consisting of an elastomeric film, a foam, and a multi-layer film.

3. The three-dimensional highly elastic film/non-woven composite of claim 1, wherein:

said first non-woven layer and said second non-woven layer are comprised of bicomponent fibers that have at least two distinct meltpoints.

4. The three-dimensional highly elastic film/non-woven composite of claim 1, wherein:

said first non-woven layer and said second non-woven layer are comprised of blended fibers that have at least two distinct meltpoints.

5. The three-dimensional highly elastic film/non-woven composite of claim 1, wherein:

said first non-woven layer and said second consolidated layer are comprised of unidirectional fibers and non-unidirectional fibers; and said first non-woven layer is comprised of fibers that are anisotropic.

6. The three-dimensional highly elastic film/non-woven composite of claim 1, wherein:

said first consolidated layer and said second consolidated layer are comprised of unidirectional fibers and non-unidirectional fibers; and said second consolidated layer is comprised of fibers that are anisotropic.

7. The three-dimensional highly elastic film/non-woven composite of claim 1, wherein:

said weld points occupy between about 2% to about 10% of a total surface area of the film/non-woven composite.

8. The three-dimensional highly elastic film/non-woven composite of claim 1, further comprising:

membranes formed in said weld points wherein said membranes rupture to form apertures when the composite is stretched in a transverse direction to an elongation greater than about 50%.

9. The three-dimensional highly elastic film/non-woven composite of claim 1, wherein:

the composite provides sufficient resistance to forces greater than about 1500 grams per inch to prevent tearing of the composite.

10. The three-dimensional highly elastic film/non-woven composite of claim 1, wherein:

the composite has an ultimate tensile direction elongation percentage in the range of about 400% to about 650%.

11. The three-dimensional highly elastic film/non-woven composite of claim 1, further comprising:

stretchable regions and non-stretchable regions.

12. The three-dimensional highly elastic film/non-woven composite of claim 1, wherein:

said first non-woven layer and said second non-woven layer are comprised of unidirectional fibers and non-unidirectional fibers; and said unidirectional and non-unidirectional fibers of said first non-woven layer have a tensile to break ratio in a machine direction to a cross direction in the range of about 3:1 to about 1.8:1.

13. The three-dimensional highly elastic film/non-woven composite of claim 1, wherein:

said first non-woven layer and said second non-woven layer are comprised of unidirectional fibers and non-unidirectional fibers; and wherein a tensile to break ratio for said unidirectional and non-unidirectional fibers in a machine direction to a cross direction of said first non-woven layer is about 1.8:1.

14. The three-dimensional highly elastic film/non-woven composite of claim 1, wherein:

said first non-woven layer and said second non-woven layer are comprised of unidirectional fibers and non-unidirectional fibers; and wherein a tensile to break ratio for said unidirectional and non-unidirectional fibers in a machine direction to a cross direction of said first non-woven layer is about 3:1.

15. The three-dimensional highly elastic film/non-woven composite of claim 1, wherein:

said first non-woven layer and said second non-woven layer are comprised of unidirectional fibers and non-unidirectional fibers; and wherein the tensile to break ratio for said first non-woven layer for a machine direction to a cross direction is about 1.8:1.

16. The three-dimensional highly elastic film/non-woven composite of claim 1, wherein:

the tensile to break ratio forces of said first non-woven layer in a machine direction to a cross direction is about 3:1.

17. A three-dimensional highly elastic film/non-woven composite, comprising:

a fluid and air impervious core film layer having a first side and a second side;

a first non-woven layer point bonded by a plurality of weld points to said first side of said core layer, said first non-woven layer having unidirectional fibers and non-unidirectional fibers, wherein said unidirectional and non-unidirectional fibers of said first non-woven layer have a tensile to break ratio for a machine direction to a cross direction in the range of about 3:1 to about 1.8:1;

a second non-woven layer point bonded by a plurality of weld points to said second side of said core layer, said second non-woven layer having unidirectional fibers and non-unidirectional fibers; and a plurality of bond regions formed by said weld points that bond said first non-woven layer, said second non-woven layer and said core layer together;

inelastic membranes within said bond regions, said membranes adapted to tear upon stretching of the composite, thereby forming apertures.

18. The three-dimensional highly elastic film/non-woven composite of claim 17, wherein:

the unidirectional fibers and non-unidirectional fibers have a tensile to break ratio of a machine direction to a cross direction in the range of about 3:1 to about 1.8:1, wherein the unidirectional fibers of said second consolidated layer are oriented in the same direction as the unidirectional fibers of said first consolidated layer fibers.

19. The three-dimensional highly elastic film/non-woven composite of claim 5, wherein:

said first consolidated layer is comprised of bicomponent fibers that have at least two distinct meltpoints.

20. The three-dimensional highly elastic film/non-woven composite of claim 5, wherein:

said first consolidated layer is comprised of blended fibers that have at least two distinct meltpoints.

21. The three-dimensional highly elastic film/non-woven composite of claim 1, wherein: the weld points rupture to form apertures when the composite is stretched in a cross-machine direction to an elongation of at least about 20%.

* * * * *

UNITED STATES PATENT AND TRADEMARK OFFICE
CERTIFICATE OF CORRECTION

PATENT NO. : 6,537,930 B1
DATED : March 25, 2003
INVENTOR(S) : Jeffrey A. Middlesworth et al.

It is certified that error appears in the above-identified patent and that said Letters Patent is hereby corrected as shown below:

<u>Title page,</u>
Item [75], Inventors, replace "Jeff" with -- Jeffrey -- and replace "Steve" with
-- Stephen --
Item [56], References Cited, OTHER PUBLICATIONS, replace "P0152" with
-- P0512 --
U.S. PATENT DOCUMENTS, replace "5,599,366" with -- 5,559,366 --

<u>Column 3,</u>
Line 1, replace "an" with -- a --

<u>Column 4,</u>
Line 58, replace "off" with -- of --

<u>Column 5,</u>
Line 6, after "to" delete "a"
Line 40, after "in" delete "an"
Line 41, insert a space between "Next," and "the"

Signed and Sealed this

Eleventh Day of May, 2004

JON W. DUDAS
*Acting Director of the United States Patent and Trademark Office*